United States Patent
Cha et al.

(10) Patent No.: US 10,113,004 B2
(45) Date of Patent: Oct. 30, 2018

(54) METHOD FOR PRODUCING DRIED BIO CELLULOSE

(75) Inventors: Jae Young Cha, Jeonbuk (KR); Sang Min Shin, Seo-gu Daejeon (KR); Mi Ae Moon, Jeonbuk (KR); Seung Gyu Kim, Gyeonggi-do (KR)

(73) Assignee: YOUCEL CO., LTD., Iksan-si Jeonbuk (KR)

( * ) Notice: Subject to any disclaimer, the term of this patent is extended or adjusted under 35 U.S.C. 154(b) by 1038 days.

(21) Appl. No.: 14/388,638

(22) PCT Filed: Mar. 30, 2012

(86) PCT No.: PCT/KR2012/002361
§ 371 (c)(1),
(2), (4) Date: Dec. 18, 2014

(87) PCT Pub. No.: WO2013/111927
PCT Pub. Date: Aug. 1, 2013

(65) Prior Publication Data
US 2015/0158954 A1 Jun. 11, 2015

(30) Foreign Application Priority Data
Jan. 26, 2012 (KR) .................. 10-2012-0007705

(51) Int. Cl.
| | | |
|---|---|---|
| *C08B 15/00* | (2006.01) | |
| *C08B 1/00* | (2006.01) | |
| *A61K 8/73* | (2006.01) | |
| *A61Q 19/00* | (2006.01) | |
| *C08L 1/02* | (2006.01) | |
| *A61K 36/258* | (2006.01) | |
| *A61K 47/38* | (2006.01) | |
| *A61K 8/02* | (2006.01) | |

(52) U.S. Cl.
CPC ............ *C08B 15/00* (2013.01); *A61K 8/0241* (2013.01); *A61K 8/731* (2013.01); *A61K 36/258* (2013.01); *A61K 47/38* (2013.01); *A61Q 19/00* (2013.01); *C08B 1/00* (2013.01); *C08L 1/02* (2013.01); *A61K 2800/10* (2013.01); *A61K 2800/41* (2013.01); *A61K 2800/80* (2013.01)

(58) Field of Classification Search
None
See application file for complete search history.

(56) References Cited

U.S. PATENT DOCUMENTS

| | | |
|---|---|---|
| 7,709,631 B2 | 5/2010 | Harris et al. |
| 2007/0197779 A1 | 8/2007 | Yang et al. |
| 2007/0213522 A1 | 9/2007 | Harris et al. |
| 2007/0231271 A1 | 10/2007 | De Souza |

FOREIGN PATENT DOCUMENTS

| | | | |
|---|---|---|---|
| JP | 09-040703 | | 2/1997 |
| JP | 09-040703 A | | 2/1997 |
| JP | 09-165402 | | 6/1997 |
| JP | 09-165402 A | * | 6/1997 |
| JP | H11-172115 A | * | 6/1999 |
| JP | 2009-530440 | | 8/2009 |
| JP | 2009-530440 A1 | | 8/2009 |
| JP | 2010-260806 A | * | 11/2010 |
| WO | WO 89/12107 | | 12/1989 |
| WO | WO 01/05838 | | 1/2001 |
| WO | WO 2007/064772 | | 6/2007 |
| WO | WO 2007/106251 | | 9/2007 |
| WO | WO 2011/079380 | | 7/2011 |

OTHER PUBLICATIONS

Notice of Preliminary Rejection in Korean Application No. 2012-0007705 dated Aug. 21, 2013.
Written Opinion and English language translation in PCT/KR2012/002361 dated Oct. 23, 2012.
PCT Search Report and English language translation in PCT/KR2012/002361 dated Oct. 23, 2012.
International Search Report for PCT/KR2012/002361 dated Oct. 23, 2012.
Written Opinion of the International Searching Authority for PCT/KR2012/002361 dated Oct. 23, 2012.
Chinese Office Action issued in Application No. 201280071870.7 dated Nov. 4, 2015 (Chinese-language only).
Extended European Search Report issued in Application No. 12866883.7 dated Sep. 25, 2015.
Fei et al, "Research Status and Prospect of Bacterial Cellulose as New Type of Nano-biomaterial." *China Pulp & Paper*, 2009, vol. 28, No. 3, pp. 56-61 (w/ abstract).
Yuan-Yuan et al., "Performance Improvement for Biomedical Material-Bacterial Cellulose," *Journal of Tianjin University of Science & Technology*, Dec. 2009, vol. 24, No. 6m, pp. 16-19 (w/ translation).

* cited by examiner

*Primary Examiner* — Susan Hoffman
(74) *Attorney, Agent, or Firm* — Nixon & Vanderhye PC

(57) ABSTRACT

The present invention provides a method for producing dried bio-cellulose which, according to one embodiment of the present invention, prevents contamination caused by microorganisms during the transport and production processes, does not require an additional anti-microorganism system in the production process, and can reduce the cost of transport and production by being stored at room temperature for a long time. Also, according to one embodiment of the present invention, the dried bio cellulose can be used as a cosmetic or pharmaceutical material for delivering medicinal substances through prompt gelation in several seconds or minutes.

5 Claims, 2 Drawing Sheets

[Fig. 1]
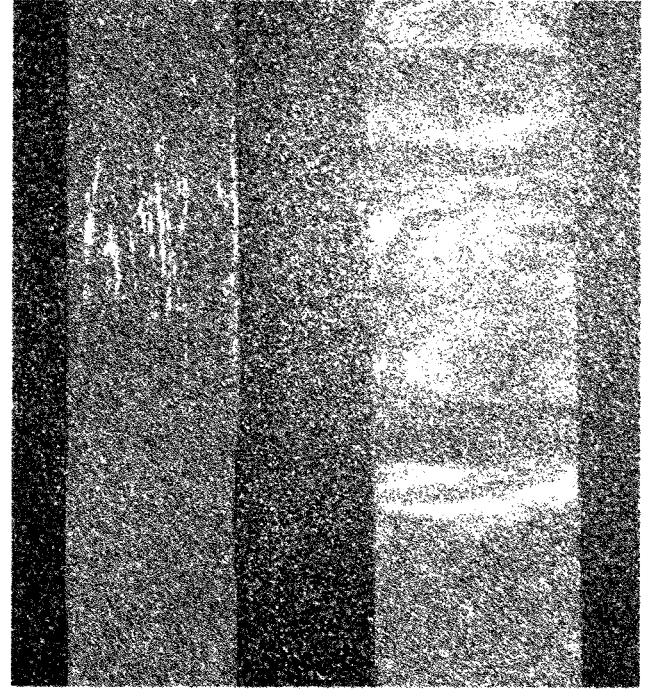
(a)        (b)
[Fig. 2]
(a)        (b)

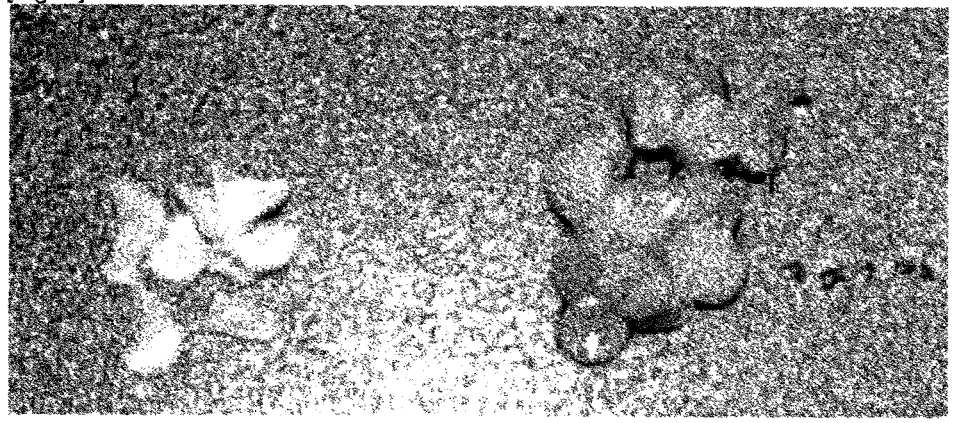
[Fig. 3]

METHOD FOR PRODUCING DRIED BIO CELLULOSE

This application is the U.S. national phase of International Application No. PCT/KR2012/002361 filed 30 Mar. 2012 which designated the U.S. and claims priority to Korean Patent Application No. KR 10-2012-0007705 filed 26 Jan. 2012 the entire contents of each of which are hereby incorporated by reference.

TECHNICAL FIELD

The present invention relates to a method for producing dry bio-cellulose, and more particularly, to a method for producing a dry bio-cellulose that is quickly gelled when water is added thereto.

BACKGROUND ART

Cellulose is an organic compound that is the second most abundant in nature next to coal. It is the main component of the cell walls of higher plants. Cotton has a cellulose content of 98%, and fibers such as flax hemp fiber and hemp fiber have a cellulose content of about 70%. Cellulose is a straight-chain polymer compound, and the purest cellulose can be obtained by degreasing cotton fibers and boiling the degreased cotton fibers in dilute alkaline aqueous solution and is a white, odorless, water-insoluble solid. Large numbers of cellulose molecules form fibers composed of micelles that have a crystalline structure having a diameter of 0.05 nm or more and a length of 0.6 nm or more. The micelles are connected to each other by amorphous regions.

Unlike plant-derived cellulose, bio-cellulose produced by microorganisms or microbial cellulose does not contain impurities such as lignin or hemicellulose other than cellulose. Bio-cellulose is based on β-1,4 glucan and has a three-dimensional network structure composed of fibrils having a diameter of 20-50 nm. Owing to this structure, bio-cellulose has wetting properties, water absorbing properties, high strength and high resilience. In addition, bio-cellulose can be used as advanced materials, such as high-strength industrial materials, composite fibers, medical materials, and enzyme immobilization materials, by improving the productivity of bio-cellulose-producing strains and establishing the genetic manipulation conditions and culture conditions of the strains.

This bio-cellulose is based on glucose, and thus is likely to be contaminated by fungi or bacteria, which include cellulase genes, during transport and production. For this reason, it is difficult to use this bio-cellulose for industrial purposes. To facilitate transport and production and prevent contamination, dry bio-cellulose has been used. However, the time required to gel dry bio-cellulose is from several hours to several days depending on the content of cellulose. Thus, there has been a need for the development of a dry bio-cellulose that is quickly gelled.

DISCLOSURE

Technical Problem

It is an object of the present invention to provide a method for producing a dry bio-cellulose that can be gelled within a short time after drying.

Technical Solution

A method for producing dry bio-cellulose according to an embodiment of the present invention includes the steps of: preparing bio-cellulose; soaking or immersing the bio-cellulose in a solution containing a glycol-based compound; and drying the soaked bio-cellulose.

The glycol-based compound may be 1,3-butylene glycol, glycerol, or propylene glycol.

The bio-cellulose may be soaked or immersed in the solution containing the glycol-based compound for 1 minute to 24 hours.

The soaked bio-cellulose may be dried at a temperature between −50° C. and 70° C. for 10 minutes to 72 hours.

The solution containing the glycol-based compound may further contain at least one medicinal component selected from the group consisting of plant extracts, vitamins and antioxidants.

The method may further comprise a step of grinding the dried bio-cellulose to a size of 0.01-300 mm.

A dry bio-cellulose according to another embodiment of the present invention is produced by a method including the steps of: preparing bio-cellulose; soaking or immersing the bio-cellulose in a solution containing a glycol-based compound; drying the soaked or immersed bio-cellulose; and mixing the glycol-based compound with water or ethanol, and is gelled by exposure to or contact with water for 1 second to 60 minutes.

The dry bio-cellulose may contain at least one medicinal component selected from the group consisting of plant extracts, vitamins and antioxidants.

Advantageous Effects

A method for producing dry bio-cellulose according to an embodiment of the present invention can prevent the dry bio-cellulose from being contaminated by microorganisms during transport and production, unlike commercially available or conventionally used water-containing cellulose. Thus, the dry bio-cellulose does not require a separate antimicrobial system during production, and can be stored at room temperature for a long period of time, and thus the transport and production costs of the dry bio-cellulose can be reduced.

In addition, a dry bio-cellulose according to an embodiment of the present invention can be quickly gelled within several seconds to several minutes. Moreover, a medicinal material may be added to the dry bio-cellulose during gelling so as to be absorbed into the cellulose, so that the bio-cellulose can be used as a cosmetic or medical material that delivers the medicinal material.

DESCRIPTION OF DRAWINGS

FIG. 1 is a photograph showing a bio-cellulose according to an embodiment of the present invention, soaked in a glycol-based compound, and the bio-cellulose after drying.

FIG. 2 is a photograph showing a dry bio-cellulose according to an embodiment of the present invention, before and after treatment with distilled water.

FIG. 3 is a photograph showing a dry bio-cellulose containing a medicinal component according to an embodiment of the present invention, before and after treatment with distilled water.

BEST MODE

Hereinafter, a method for producing a dry bio-cellulose according to an embodiment of the present invention and a dry bio-cellulose will be described in detail.

A method for producing dry bio-cellulose according to an embodiment of the present invention comprises the steps of: preparing bio-cellulose; soaking or immersing the bio-cellulose in a solution containing a glycol-based compound; and drying the soaked or immersed bio-cellulose.

The bio-cellulose that is used in the present invention may be bio-cellulose produced by bio-cellulose-producing microorganisms. In an embodiment of the present invention, the bio-cellulose may be a mandarin gel, produced according to the disclosure of Korean Patent Application No. 2010-0085634 (entitled "Method for preparing cellulose gel using novel *Gluconacetobacter* sp. strain isolated from mandarin juice; developed by the Korean Rural Development Administration), or bio-cellulose produced by inoculating *Acetobacter xylinum* into coconut produced by a traditional method used in Southeast Asia. The bio-cellulose may be a sheet-type or ground bio-cellulose, but is preferably a sheet-type bio-cellulose for the convenience of the process. Also, the bio-cellulose is used after it is sufficiently dewatered in a centrifuge for 10 minutes or more, so that the glycol-based compound can be easily absorbed into the bio-cellulose.

The glycol-based compound that is used in the present invention may be 0.1-10% 1,3-butylene glycol, glycerol, propylene glycol or the like. As a solvent for the glycol-based compound, distilled water or ethanol may be used. The glycol-based compound is added to distilled water or ethanol in an amount of 0.1-50 parts by weight based on 100 parts by weight of distilled water or ethanol to a glycol-based compound solution. The glycol-based compound solution is absorbed into the dewatered bio-cellulose by a method such as soaking or spraying. When the bio-cellulose is to be soaked in the glycol-based compound solution, it is preferably soaked at room temperature for 1 minute or more.

In an embodiment of the present invention, the solution containing the glycol-based compound may further contain 0.1-50 parts by weight of a medicinal component in order to use the bio-cellulose for cosmetic or medical purposes. Herein, the medicinal component is added by taking into consideration the fact that the medicinal component is diluted during drying or gelling after drying. The medicinal component is absorbed into the skin through the bio-cellulose to exhibit beneficial effects in the skin, and may be selected from among various plant extracts, vitamins such as vitamin C and vitamin E, and antioxidants such as hyaluronic acid.

FIG. 1 is a photograph showing a bio-cellulose according to an embodiment of the present invention, soaked or immersed in a glycol-based compound, and the bio-cellulose after drying.

FIG. 1(*a*) shows the soaked bio-cellulose before drying, and FIG. 1(*b*) shows the bio-cellulose after drying. The soaked or immersed bio-cellulose may be dried at a temperature between −50° C. and 70° C. for 10 minutes to 72 hours by the use of a drying method, such as freeze drying, hot-air drying, oven drying or natural drying. Herein, the bio-cellulose is preferably dried in a state in which it is supported on nonwoven fabric or a mesh-type plastic plate, so that air can move to the bio-cellulose, water can be easily removed from the bio-cellulose, and the bio-cellulose does not fold or overlap.

The method may further comprise a step of grounding or cutting the dried bio-cellulose to a size of 0.01-300 mm in order to facilitate transport and storage. The dried bio-cellulose may be ground by taking into consideration the size that is obtained when the dried bio-cellulose is gelled in order to use it for cosmetic, food or medical purposes. The dried bio-cellulose may be ground into powder using a grinder, and cut into a square or circular shape.

A dry bio-cellulose according to another embodiment of the present invention is produced by a method comprising the steps of: preparing bio-cellulose; soaking or immersing the bio-cellulose in a solution containing a glycol-based compound; drying the soaked or immersed bio-cellulose; and mixing the glycol-based compound with water or ethanol, and is gelled by exposure to or contact with water for 1 second to 60 minutes.

The method for preparing the dry bio-cellulose is the same as the above-described method, and thus the detailed description is omitted to avoid overlapping.

FIG. 2 is a photograph showing a dry bio-cellulose according to an embodiment of the present invention, before and after treatment with distilled water.

FIG. 2(*a*) shows a dry bio-cellulose, and FIG. 2(*b*) shows a bio-cellulose gelled by soaking or immersing in distilled water or the like. The dry bio-cellulose can be gelled by treating it with an excess of distilled water for 1 second to 60 minutes. The dry bio-cellulose can be gelled by soaking or immersing it in distilled water or spraying it with distilled water. It can be seen that the gelled bio-cellulose was restored to the same state as that of the bio-cellulose (before drying) shown in FIG. 1(*a*).

FIG. 3 is a photograph showing a dry bio-cellulose containing a medicinal component according to an embodiment of the present invention, before and after treatment with distilled water.

Referring to FIG. 3, a dry bio-cellulose according to an embodiment of the present invention may contain medicinal components such as plant extracts, vitamins or vitamins. The medicinal components are absorbed into the skin through the bio-cellulose to exhibit beneficial effects in the skin, and may be various plant extracts, vitamins such as vitamin C and vitamin E, and antioxidants such as hyaluronic acid.

Hereinafter, the present invention will be described in further detail with reference to examples. It is to be understood, however, that these examples are for illustrative purposes only and are not intended to limit the scope of the present invention.

EXAMPLES

Example 1: Production 1 of Dry Bio-Cellulose 100 g of a mandarin gel, produced according to the disclosure of Korean Patent Application No. 2010-0085634 (entitled "Method for preparing cellulose gel using novel *Gluconacetobacter* sp. strain isolated from mandarin juice; developed by the Korean Rural Development Administration), was dewatered in a centrifuge for 10 minutes. The dewatered mandarin gel was soaked or immersed in a solution of 25 ml of 1,3-butylene glycol in 75 ml of distilled water at room temperature for 1 minute or more such that 1,3-butylene glycol was sufficiently absorbed into the mandarin gel. The mandarin gel was dried in a dryer for 2 hours to prepare a dry bio-cellulose. During drying, the bio-cellulose was supported on nonwoven fabric or a mesh-type plastic plate such that air and water could move.

Example 2: Production 2 of Dry Bio-Cellulose 100 g of the same mandarin gel as described in Example 1 was dewatered in a centrifuge for 10 minutes. The dewatered mandarin gel was soaked or immersed in a solution of 25 ml of glycerol in 75 ml of distilled water at room temperature for 1 minute or more such that glycerol was sufficiently absorbed into the mandarin gel. The mandarin gel was dried in a dryer for 2 hours to prepare a dry bio-cellulose. During drying, the bio-cellulose was supported on nonwoven fabric or a mesh-type plastic plate such that air and water could move.

Example 3: Production 3 of Dry Bio-Cellulose 100 g of the same mandarin gel as described in Example 1 was dewatered in a centrifuge for 10 minutes. The dewatered mandarin gel was soaked or immersed in a solution of 25 ml of propylene glycol in 75 ml of distilled water at room temperature for 1 minute or more such that propylene glycol was sufficiently absorbed into the mandarin gel. The mandarin gel was dried in a dryer for 2 hours to prepare a dry bio-cellulose. During drying, the bio-cellulose was supported on nonwoven fabric or a mesh-type plastic plate such that air and water could move.

Example 4: Production 4 of Dry Bio-Cellulose 100 g of the same mandarin gel as described in Example 1 was dewatered in a centrifuge for 10 minutes. The dewatered mandarin gel was soaked or immersed in a solution of 25 ml of 1,3-butylene glycol in 75 ml of ethanol at room temperature for 1 minute or more such that 1,3-butylene glycol was sufficiently absorbed into the mandarin gel. The mandarin gel was dried in a dryer for 2 hours to prepare a dry bio-cellulose. During drying, the bio-cellulose was supported on nonwoven fabric or a mesh-type plastic plate such that air and water could move.

Example 5: Production 5 of Dry Bio-Cellulose 100 g of a bio-cellulose, produced by inoculating *Acetobacter xylinum* into coconut produced by a traditional method used in Southeast Asia, was dewatered in a centrifuge for 10 minutes. The dewatered mandarin gel was soaked or immersed in a solution of 25 ml of 1,3-butylene glycol in 75 ml of distilled water at room temperature for 1 minute or more such that 1,3-butylene glycol was sufficiently absorbed into the mandarin gel. The mandarin gel was dried in a dryer for 2 hours to prepare a dry bio-cellulose. During drying, the bio-cellulose was supported on nonwoven fabric or a mesh-type plastic plate such that air and water could move.

Example 6: Production of Dry Bio-Cellulose Containing Medicinal Component 100 g of the same mandarin gel as described in Example 1 was dewatered in a centrifuge for 10 minutes. 1 g of a ginseng extract was mixed with 74 ml of distilled water, and then mixed with 25 ml of 1,3-butylene glycol. The dewatered mandarin gel was soaked or immersed in the mixture for 1 minute or more such that the components of the mixture were sufficiently absorbed into the mandarin gel. The mandarin gel was dried in a dryer for 2 hours to prepare a dry bio-cellulose. During drying, the bio-cellulose was supported on nonwoven fabric or a mesh-type plastic plate such that air and water could move.

The invention claimed is:

1. A method for producing dry bio-cellulose, the method comprising the steps of:
   providing a bio-cellulose;
   dewatering the bio-cellulose in a centrifuge for 10 minutes or more;
   immersing the dewatered bio-cellulose in a solution containing a glycol-based compound; and
   supporting the immersed bio-cellulose on nonwoven fabric or a mesh-type plastic plate and drying the supported bio-cellulose,
   wherein the glycol-based compound is 1,3-butylene glycol, and
   wherein the solution containing the glycol-based compound has an amount of 0.1-50 parts by weight of the glycol-based compound based on 100 parts by weight of the solution.

2. The method of claim 1, wherein the dewatered bio-cellulose is immersed in the solution containing the glycol-based compound for 1 minute to 24 hours.

3. The method of claim 1, wherein the supported bio-cellulose is dried at a temperature between −50° C. to 70° C. for 10 minutes to 72 hours.

4. The method of claim 1, wherein the solution containing the glycol-based compound further comprises at least one medicinal component selected from the group consisting of plant extracts, vitamins and antioxidants.

5. The method of claim 1, further comprising a step of grinding or cutting the dried bio-cellulose to a size of 0.01-300 mm.

* * * * *